United States Patent [19]

Gellert et al.

[11] 3,955,577
[45] May 11, 1976

[54] RESIN TREATED ABSORBENT PAD OR WEB FOR BODY FLUIDS

[75] Inventors: Dale A. Gellert, Aurora, Ind.; Kendall L. Harden; John R. Noel, both of Cincinnati, Ohio

[73] Assignee: The Procter & Gamble Company, Cincinnati, Ohio

[22] Filed: Feb. 18, 1975

[21] Appl. No.: 550,799

Related U.S. Application Data

[62] Division of Ser. No. 452,095, March 18, 1974, Pat. No. 3,901,238.

[52] U.S. Cl. ............................ 128/290 R; 128/287; 128/284
[51] Int. Cl.² .......................................... A61F 13/16
[58] Field of Search ............... 128/284, 287, 290 R, 128/296; 428/288, 474, 522, 131, 224, 289

[56] References Cited
UNITED STATES PATENTS

| | | | |
|---|---|---|---|
| 3,017,304 | 1/1962 | Burgeni | 128/290 R |
| 3,339,550 | 9/1967 | Van Haaften | 128/290 R |
| 3,444,859 | 5/1969 | Kalwaites | 128/284 |
| 3,523,536 | 8/1970 | Ruffo | 128/287 |
| 3,612,055 | 10/1971 | Mesek | 128/287 |
| 3,663,348 | 5/1972 | Liloia | 128/284 X |
| 3,687,712 | 8/1972 | Hartman | 128/290 R X |
| 3,721,242 | 3/1973 | Krusko | 128/287 |
| 3,779,246 | 12/1973 | Mesek | 128/287 |
| 3,903,890 | 9/1975 | Mesek | 128/287 |

Primary Examiner—Aldrich F. Medbery
Attorney, Agent, or Firm—E. Kelly Linman; Fredrick H. Braun; John V. Gorman

[57] ABSTRACT

A disposable diaper combining improved softness and sufficient strength to resist in use tearing and shredding in a single structure, thereby producing better compliance and fit when the structure is applied to the wearer, and hence improved comfort as well as better containment of waste fluids deposited thereon. In a preferred embodiment, a disposable diaper of the present invention employs an air laid absorbent cellulosic core reinforced by the application of a hydrophobic resin at relatively low levels of solids addition to one side thereof with subsequent drying, curing and calendering to the desired overall density. With sufficient strength built into the resin treated surface of the absorbent core structure, the unreinforced surface of the absorbent core can be adhered directly to a soft, waterproof backsheet, thereby producing a unique softness, texture and hand. In addition to improved strength and softness, a resin-stabilized absorbent core of the present invention exhibits improved surface dryness due to favorable density and capillary gradients which provide improved liquid penetration from the resin treated surface of the core to the non-resin treated portions of the core. By combining the resin-stabilized absorbent core with a fast strike-through topsheet in a disposable diaper structure, the gasket-like waterproof side flaps normally required to prevent liquid run-off can be eliminated.

10 Claims, 7 Drawing Figures

RESIN TREATED ABSORBENT PAD OR WEB FOR BODY FLUIDS

This application is a division of application Ser. No. 452,095 filed Mar. 18, 1974 and now U.S. Pat. No. 3,901,238.

FIELD OF THE INVENTION

The present invention has relation to disposable absorbent products generally, and in particular to disposable absorbent products such as bandages, diapers and sanitary napkins.

In a preferred embodiment, the present invention has relation to a resin-stabilized absorbent cellulosic web suitable for use in disposable absorbent products, said web having improved softness and strength as well as favorable density and capillary gradients to provide improved liquid penetration and retention characteristics between the resin treated surface of the web and the non-resin treated portions thereof.

In yet another preferred embodiment, the present invention has relation to a disposable diaper exhibiting improved softness, texture and hand as well as sufficient strength to resist tearing or shredding of the absorbent pad in use, thereby providing greater wearer comfort and better absorbency along with improved containment due to better fit.

In still another preferred embodiment, the present invention has relation to a disposable diaper exhibiting both improved surface dryness and more rapid strike-through of fluids deposited on the surface of said diaper, thereby eliminating the need for gasketing means along the lateral edge portions of said structure to prevent liquid run-off during periods of heavy flow.

BACKGROUND OF THE INVENTION

Disposable absorbent products, and particularly disposable absorbent bandages, diapers and sanitary napkins are well known. An object common to such products is the provision of an effective means for absorbing aqueous liquids such as urine deposited thereon in such a manner as to prevent run-off during maximum flow conditions and to effectively retain such liquids absorbed within the absorbent core member of the structure. It is likewise an object of such structures to reduce the amount of moisture in contact with the wearer's skin and thus reduce maceration, rash or other unpleasantness. Such structures should preferably exhibit both strength and softness to enhance their absorbency and containment characteristics in addition to wearer comfort. Prior art disposable absorbent products have not, however, successfully combined all of the aforementioned desirable features in a single structure.

Structures comprised of a porous hydrophobic topsheet and a hydrophilic substrate are well known in the art. It should be recognized that the terms "hydrophobic" and hydrophilic as herein employed, while useful in their brevity actually refer, respectively to relatively low and relatively high critical surface tensions of the materials being characterized. The hydrophobic nature of a prior art diaper topsheet, for example, is evidenced by its lack of affinity for liquid human waste relative to that of the hydrophilic or absorbent substrate. As used herein, a web is hydrophobic when a drop of liquid waste placed thereon does not spread to any appreciable degree on the web. Thus, when a hydrophobic sheet is superimposed upon a layer of hydrophilic or less hydrophobic absorbent material to form a diaper and the hydrophobic material is placed next to wearer's skin, waste fluids from the wearer pass through the hydrophobic sheet and are preferentially partitioned by and absorbed within the underlying hydrophilic layer, leaving the topsheet adjacent the wearer's skin relatively dry.

The rate at which liquid penetration takes place varies greatly, however, depending upon such factors as the density and capillary gradients existing between the various layers of the absorbent structure and the relative hydrophobicity of the various layers. Capillary forces act to draw a liquid from a less dense structure to a more dense hydrophilic structure, i.e., from a large pore size to a smaller pore size, and this directional action can be augmented further by employing a topsheet which is both lower in density and slightly hydrophobic with respect to the hydrophilic absorbent core to promote rapid absorption of the liquid deposited on the topsheet by the absorbent core member, thereby minimizing liquid run-off during periods of heavy flow. Care must be taken, however, that the surface dryness of the structure not be adversely affected. If an extremely thin, low density, hydrophobic topsheet is emoloyed in combination with a more dense hydrophilic core, fluids absorbed by the hydrophilic core may not be effectively prevented from re-emerging at the surface of the topsheet when the structure is subjected to compressive forces generated by the activities of the wearer.

In general, a more hydrophobic topsheet provides poorer strike-through characteristics but better surface dryness, while a less hydrophobic topsheet provides better strike-through characteristics but poorer surface dryness. Thus to a certain extent there has been a balancing in prior art structures between favorable strike-through characteristics and favorable surface dryness characteristics.

As used hereinafter, strike-through is a measure of how long it takes for an absorbent structure to completely absorb a specified quantity of liquid deposited on its surface. Strike-through values are normally expressed in seconds. Low strike-through values are indicative of high absorbency rates, and are, therefore, generally preferred in absorbent bandages and the like. Surface wetness, on the other hand, is a measure of the degree to which absorbed moisture can be caused to re-emerge from an absorbing matrix, under pressure, to appear as moisture at the surface of the structure where it originally entered the absorbing matrix. Surface wetness values are normally expressed in grams of re-emerging liquid absorbed on a standard filter paper superposed on the absorbing matrix. Low surface wetness values are indicative of a greater ability of the absorbent structure to retain an aqueous solution once it has been absorbed, i.e., improved surface dryness.

One prior art means of providing satisfactory surface dryness characteristics while minimizing liquid run-off is disclosed in U.S. Pat. Re. No. 26,151 which issued to Duncan et al. on Jan. 31, 1967. The Duncan et al. patent discloses a disposable diaper structure employing an absorbent pad and a waterproof backsheet of a width greater than that of the pad. The side portions of the backsheet are folded inwardly over the side marginal areas of the pad so that in use liquid runoff is minimized during periods of heavy flow. The inwardly folded side portions assume a position contiguous to the wearer's legs along an area of the inner, rear and front portions of the thighs adjacent the junction thereof with the wearer's torso, thus providing a gasketing action. In the described embodiment, a hydrophobic topsheet encloses the absorbent material of the pad. The gasketing action gives the absorbent pad sufficient time to absorb liquid wastes to thus utilize, as fully as possible, the absorptive power of the diaper while simultaneously preventing run-off during periods of heavy flow and consequent soiling of garments.

While side flaps have proven to be one acceptable solution to the run-off problem in a disposable diaper exhibiting satisfactory surface dryness characteristics, applicants' invention, in a preferred embodiment, provides rapid strike-through and improved surface dryness characteristics in a single structure, thus making the use of side flaps to prevent liquid run-off unnecessary. Applicants' structure is, therefore, simpler in terms of construction as well as in its application to the wearer.

Another problem common to most prior art disposable absorbent structures relates to a lack of strength in the absorbent core materials employed. This problem is particularly apparent with airfelt, an air laid cellulosic material which is widely used in disposable absorbent products due to its desirable absorbency and softness characteristics and its relatively low cost. Disposable absorbent products, and particularly disposable diapers fabricated with absorbent cores of unreinforced airfelt do not, however, have sufficient strength to resist tearing and shredding in use. Tearing and shredding of the absorbent core in a disposable diaper is undesirable in that it adversely affects both the absorbency and containment characteristics of the structure in addition to being aesthetically unacceptable to the consumer. Prior art disposable absorbent products have dealt with this problem by various means, including, for example, wet calendering of the airfelt, wet-strength tissue addition, embossing of the airfelt, addition of adhesive strips to the airfelt, etc.

U.S. Pat. No. 3,612,055 which issued to Mesek et al. on Oct. 12, 1971 discloses a disposable diaper having an absorbent core of loosely compacted cellulosic batt having greater wettability than that of the facing web, said batt having a highly compacted layer on its back side which is adhered directly to a waterproof backing sheet over a widely distributed area of adhesion. The densified surface is produced by calendering the absorbent web while the surface to be densified is in a moist condition. Liquid deposited on the surface of the structure disclosed by Mesek et al. passes through the body of the loosley compacted batt and is strongly drawn into the densified layer due to the small capillary radius of the of the densified fibers. Such a diaper, although effective from a liquid absorption and liquid retention standpoint, has a rather stiff feel due to the fact that the densified layer of the absorbent core is in adherent contact with the waterproof backsheet, thereby tending to impart the stiffness of the absorbent core to the entire structure.

U.S. Pat. No. 3,444,859 which issued to Kalwaites on May 20, 1969 discloses alternative means for reinforcing a fibrous batt to impart mechanical strength thereto by foam bonding the exterior surfaces of the batt to form a relatively strong skin thereon. The skin on the exterior surfaces of the batt, however, detracts from the softness and texture of a disposable diaper structure incorporating the batt as an absorbent core.

OBJECTS OF THE INVENTION

Accordingly, it is an object of the present invention to provide a resin-reinforced absorbent web of air laid cellulosic material exhibiting sufficient strength to resist tearing and shredding when used in absorbent products such as disposable diapers, yet retaining much of the softness inherent in such materials prior to the application of any reinforcing treatment.

It is a further object of the present invention to provide an absorbent pad of compressed, entangled, hydrophilic fibers, the fibers on one surface thereof being treated in the uncompressed state with a hydrophobic film-forming material which acts as an interfiber bond inhibitor and a fiber stiffener during compression, which pad, after compression, exhibits favorable density and capillary gradients to promote wicking of liquid from the treated surface of the absorbent pad to the untreated portions thereof.

It is yet another object of the present invention to provide a disposable diaper having greater wearer comfort due to improved softness, texture and hand as well as sufficient strength to resist tearing and shredding in use, said diaper thereby providing improved absorbency and better containment due to better fit.

Still another object of the present invention is to provide a soft, compliant disposable diaper exhibiting strike-through characteristics sufficiently rapid to substantially prevent liquid run-off during periods of heavy flow as well as improved surface dryness characteristics.

SUMMARY OF THE INVENTION

In accordance with the present invention, an absorbent fibrous web suitable for use as an absorbent core in disposable absorbent products is provided, said web comprising a compressed mass of entangled hydrophilic fibers, the fibers on one surface thereof being treated by the addition of a film-forming, hydrophobic resin at relatively low levels of solids addition while said web is in an uncompressed state, with drying and curing of said resin treated web in the uncompressed state followed by subsequent calendering of said web to the desired overall density. The resin acts as an interfiber bond inhibitor and fiber stiffener during compression so that the treated portions of the absorbent web remain at a lower density after calendering than the untreated portions, thereby creating a favorable density and capillary gradient between the resin treated surface and the untreated portions of the web. Because of the hydrophobic nature of the resin, the favorable gradients are maintained when moisture is deposited on the structure, thus providing improved surface dryness on the resin treated surface of the web. In addition, the resin treatment imparts sufficient strength to the absorbent web to resist in use tearing and shredding when the web is employed as an absorbent core in an absorbent structure such as a disposable diaper.

In a preferred embodiment, an absorbent web of the present invention is incorporated in a disposable diaper so that the non-resin treated surface of the web is adhered directly to a soft, waterproof backsheet. Due to the inherent softness of the untreated surface of the absorbent web, a unique texture and hand which complement softness are produced, while the resin treated surface of the web provides the strength necessary to resist tearing and shredding in use. Because such a diaper exhibits improved strength and softness, better compliance and fit are achieved when the structure is applied to the wearer. This in turn provides better containment of discharged wastes and improved wearer comfort.

In yet another preferred embodiment, a fast strike-through topsheet is superimposed on the resin treated surface of an absorbent pad of the present invention and secured at its periphery to a waterproof backsheet adhered to the untreated surface of the absorbent pad to form a disposable diaper. By combining a fast strike-through topsheet with an absorbent web having favorable density and capillary gradients to rapidly transmit moisture deposited on the surface of the diaper into the untreated portions of the absorbent core, liquid run-off can substantially be prevented without resort to special restraining means at the lateral edge portions of the diaper. Such a diaper also exhibits better surface dryness than is normally obtainable when a fast strike-through topsheet is employed due to the tendency of the resin treated surface of the absorbent pad to partition liquid absorbed in the non-resin treated portions of the pad from the topsheet, at least until the full absorptive capacity of the non-resin treated portions of the pad has been utilized.

BRIEF DESCRIPTION OF THE DRAWINGS

While the specification concludes with claims particularly pointing out and distinctly claiming the subject matter which is regarded as the present invention, it is believed that the invention will be better understood from the following description taken in connection with the accompanying drawings in which:

DESCRIPTION OF THE PREFERRED EMBODIMENTS

Figures 1A, 1B:
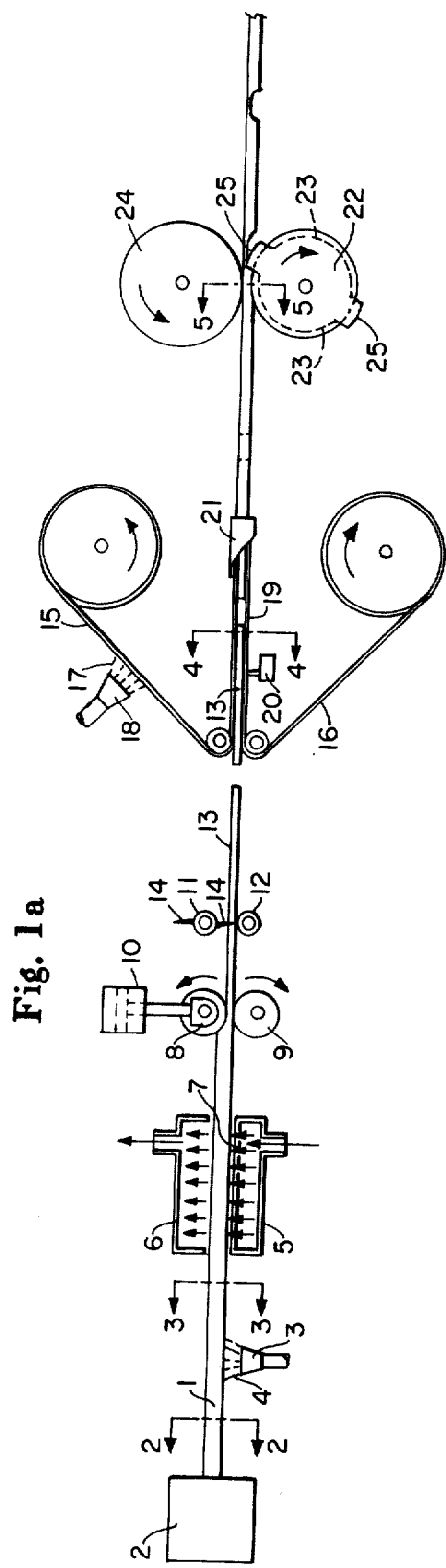
FIG. 1A is a simplified schematic illustration of a portion of a production line used for processing an absorbent fibrous web in accordance with the present invention and for converting the processed web into a disposable diaper.
FIG. 1B is a continuation of the simplified schematic illustration of FIG. 1A showing the balance of the diaper converting operation.
Figure 2:
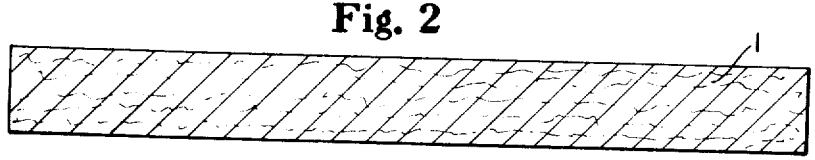
FIG. 2 is an enlarged schematic illustration of an uncompressed fibrous web shown prior to processing in accordance with the present invention, taken along section line 2—2 in FIG. 1A.

FIGS. 1A and 1B constitute a simplified schematic illustration of a production line suitable for preparing an absorbent fibrous web in accordance with the present invention and for converting said web into a disposable diaper. In a preferred embodiment of the present invention, an absorbent fibrous web 1 of hydrophilic cellulosic material is produced by conventional air laying techniques well known in the art and shown schematically as 2 in FIG. 1A. The absorbent fibrous web 1, which is commonly referred to in the industry as airfelt, preferably has an initial basis weight between about 80 and about 500 grams per square meter. The density of the web 1 typically ranges between approximately 0.03 and approximately 0.05 grams per cubic centimeter, as measured under a load of 20 grams per square centimeter, prior to processing in accordance with the present invention. As shown schematically in FIG. 2, the fibrous structure of the web is extremely loose prior to treatment in accordance with the present invention, and, therefore, the web has very little cohesive strength.

The first step designed to impart integrity and strength as well as improved surface dryness characteristics to an absorbent web of the present invention involves the application of a film-forming hydrophobic resin to one surface of the absorbent web. This is preferably accomplished by applying the liquid resin 4 with one or more spray nozzles 3 so that a substantially uniform spray extends across the entire width of the absorbent web 1.

Figure 3:
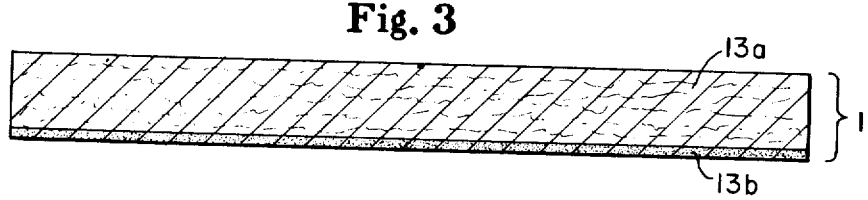
FIG. 3 is an enlarged simplified schematic illustration of the absorbent fibrous web illustrated in FIG. 2 shown after application of the reinforcing resin to the lowermost side thereof, taken along section line 3—3 in FIG. 1A.

As shown in FIG. 3, the resin 4 does not penetrate the entire thickness of the absorbent web 1. The resin treatment is limited to portion 13(b) of the absorbent web. In order to realize the surface dryness benefits of an absorbent web of the present invention, to be described in greater detail hereinafter, the untreated hydrophilic portion 13(a) of the absorbent web 1 should constitute at least about 50 percent and most preferably at least about 70 percent of the total thickness of the absorbent web prior to calendering.

The resin 4 imparts wet strength to the absorbent web by bonding the surface fibers together at contact points while the fibers are in an expanded lattice structure. Since the fibers are randomly distributed in the vertical as well as the horizontal plane and bonded only at contact points, the resulting structure remains flexible. The resin coating on the fibers also tends to prevent the formation of additional bonds between the treated fibers during subsequent calendering, thereby insuring the maintenance of flexibility in the web after calendering as well as helping to produce improved surface dryness on the resin treated surface of the web.

The resin employed is preferably moderately hard and is non-tacky when dry to avoid self-adhering when the absorbent web 1 is calendered. One such resin found to produce very good results is styrene-butadiene, a hydrophobic resin available from the Dow Chemical Company of Midland, Michigan under Dow specification number 7284.01. Other hydrophobic resins also found suitable include, for example, styrene-butadiene No. 7235 also available from the Dow Chemical Company, and an acrylic-latex resin available from the Rohm and Haas Chemical Company of Philadelphia, Pa. under Rohm and Haas specification number TR-407.

A distinguishing resin property used commonly by polymer manufacturers in characterizing a resin in its behavior as a film-forming coating is its glass transition temperature. Within a molecular weight series of a given resin the polymer is less tacky and self-adhering at higher glass transition temperatures. Thus, if after proper drying and curing of an absorbent web 1 of the present invention, the resin treated surface 13(b) self-adheres on calendering, the difficulty can frequently be avoided by selecting a resin with a higher glass transition temperature. Generally it has been found that the preferred resins fall within the glass transition temperature range of about −15°C to about +35°C.

The resin 4 is preferably applied to the absorbent web 1 at relatively low levels of solids addition, i.e., preferably between about 5 and about 16 grams of resin solids per square meter, at a solids content of between about 10 percent and about 55 percent by weight. Low levels of resin application are desirable primarily to avoid adverse effects on the softness, texture and hand of the structure.

Although it is feasible to apply a resin spray to both surfaces of the absorbent web 1, in a preferred embodiment of the present invention only one surface of the web is treated in order to preserve a sufficient amount of hydrophilic material in the web as well as the inherent softness of the web, essential features of a disposable diaper of the present invention. It should be noted that due to the inherent flexibility of the web reinforcing process described herein, it is also feasible to apply the resin 4 only in selected areas of the web for localized reinforcement as well as to vary the amount of resin applied at any given point across the web to produce varying degrees of reinforcement across the web.

Following application of the resin spray 4 to the lowermost surface of the absorbent web 1 in the uncompacted condition, the absorbent web is passed between a hot air blow-through dryer 5 and a suction box 6 which serve to drive moisture from the structure and cure the resin. Both the hot air dryer 5 and the suction box 6 extend across the entire width of the absorbent web 1. Hot air is introduced directly onto the resin treated surface of the web through a plurality of orifices 7 in the hot air dryer 5. Since the web is relatively open at this point, the bulk of the hot air passes through the absorbent web and is collected within the suction box 6 where it is continuously reheated and recycled back to the hot air dryer 5 by means well known in the art.

The hot air dryer 5 and suction box 6 are preferably designed so that the absorbent web 1 will be dried and cured upon exit therefrom. Experience has demonstrated that drying and curing can, for example, be achieved with an absorbent fibrous web having a density prior to treatment of approximately 0.05 grams per cubic centimeter as measured under a load of 20 grams per square centimeter, said web having been treated on one surface with a styrene-butadiene resin such as Dow No. 7284.01 applied at a solids content of about 10 percent and a level of approximately 11 grams of resin solids per square meter, by directing a forced convection of 270°F dry air through the web at a rate of about 450 cubic feet per minute per square foot of web surface for a period of approximately 5 seconds. Higher resin solids concentrations and/or higher drying temperatures can be utilized to reduce the residence time required to effect drying and curing.

In general, experience has demonstrated that a resin treated absorbent web 1 can normally be cured by subjecting it to a force convection of 270°F dry air for a period of time sufficient to reduce the moisture content of the structure to below about 5 percent.

An absorbent fibrous web which has been dried and cured prior to calendering exhibits improvements not only in pad integrity and tensile strength, but, in addition, provides a basis for combining improved strike-through and surface dryness characteristics in a single absorbent structure such as a disposable diaper. An absorbent fibrous web which has been dried but not cured prior to calendering, on the other hand, provides a lesser degree of surface dryness improvement.

Following the drying and curing operation, the resin-stabilized absorbent fibrous web 1 is passed between a pair of hard-surfaced calendering rolls 8 and 9 to increase the overall density of the web to the desired level. When the initial density of the structure prior to treatment in accordance with the present invention is in the range of about 0.03 to about 0.05 grams per cubic centimeter as measured under a load of 20 grams per square centimeter, the structure is normally calendered to an overall density between about 0.07 and about 0.15 grams per cubic centimeters, and most preferably to between about 0.09 and about 0.13 grams per cubic centimeter when the absorbent web 1 is to be utilized in a disposable diaper. The target density of the absorbent web is preferably controlled by adjusting the force applied to the web as it passes between the rolls. This is accomplished by mounting roll 9 in a fixed position and controlling the vertical movement of roll 8 by means of a multiplicity of pneumatically or hydraulically actuated cylinders 10 which are regulated to produce a constant compressive force on the web.

As alluded to earlier herein, the aforementioned web treatment imparts integrity, cohesiveness and tensile strength to an otherwise weak structure. As would be expected, the wet and dry tensile strengths of the absorbent web 1 are dependent to a large extent upon the level of resin application as well as upon the particular resin utilized. For a resin such as Dow No. 7284.01, solids application levels between about 5 and about 16 grams per square meter on an absorbent web having a density between about 0.03 and about 0.05 grams per cubic centimeter prior to treatment in accordance with the present invention results in wet tensile strengths between about 0.5 and about 1.5 pounds force per inch of pad width when the treated structure is calendered to a density between about 0.09 and about 0.13 grams per cubic centimeter. That is, a force of between about 0.5 and about 1.5 pounds is required to separate a 1 inch wide sample of the web which has been uniformly wetted with a quantity of simulated urine solution equal to four times the weight of the sample. The simulated urine solution is comprised of a 1 percent sodium chloride solution adjusted to a surface tension of 45 dynes per centimeter.

For use in a structure such as a disposable diaper which is subjected to considerable in use stress both wet and dry due to the action of the wearer, a minimum wet tensile strength of about 0.5 pounds force per inch of pad width, and preferably about 1.0 pounds force per inch of pad width, is desirable to resist tearing and shredding. This can normally be achieved in an absorbent pad having a basis weight of at least 80 grams per square meter and a density prior to treatment of approximately 0.03 to 0.05 grams per cubic centimeter by applying a resin such as Dow styrene-butadiene No. 7284.01 at a rate of approximately 11 grams of solids per square meter and calendering the structure after drying and curing to a density between about 0.09 and about 0.13 grams per cubic centimeter.

As disclosed earlier herein, an absorbent fibrous web 1 which has been cured prior to calendering provides a basis for improved surface dryness and strike-through characteristics in addition to improved strength and integrity when used in an absorbent structure such as a disposable diaper.

It is believed that the primary reason an absorbent fibrous web prepared as herein described exhibits improved surface dryness characteristics on its resin treated surface is due to the fact that favorable density and capillary gradients are created between the treated surface of the web and the untreated portions thereof. Because the resins employed by applicants are interfiber bond inhibitors during compression and because they impart resilience to the fibers which have been treated therewith, the resin treated surface of the web exhibits a lower density than the untreated portions of the absorbent web after calendering. In the case of an absorbent web produced as described herein, the untreated portions of the absorbent core may range from slightly more dense than the resin treated portions of the core to several times more dense than the resin treated portions of the absorbent core, depending to a large extent on the degree of calendering of the structure. In general, the more favorable the density and capillary gradients between the resin treated surface of the web and the untreated portions thereof the lower will be the surface wetness values associated therewith.

Since the absorbent web 1 is preferably comprised of hydrophilic cellulosic fibers, the resin 4, in order to maintain the favorable density and capillary gradients described above when the structure is wetted, must not only be hydrophobic in nature, but further, must be of a film-forming variety so as to encapsulate the fibers on the treated surface of the web and prevent them from becoming wetted.

Accordingly, when moisture is deposited on the resin treated surface of an absorbent fibrous web 1, the favorable density and capillary gradients existing between the resin treated surface of the structure and the untreated portions thereof serve to rapidly transmit the moisture from the resin treated surface to the untreated portions. Because the resin treated fibers of the absorbent web exhibit hydrophobic properties after the resin treatment, they are not readily wetted by liquids deposited on the resin treated portion 13(b) of the absorbent web 1. Hence the favorable density and capillary gradients existing between the treated and the untreated portions of the web are not destroyed when the structure is subjected to moisture. Liquid deposited on the resin treated surface 13(b) of the absorbent web 1 is rapidly transmitted to the absorbent hydrophilic portion of the core 13(a) until the full absorptive capacity of the latter has been exhausted. Surface wetness is also reduced, i.e., surface dryness is improved, on the resin treated surface of the web due to the tendency of liquids absorbed in the hydrophilic core to migrate preferentially throughout the hydrophilic layer rather than in the direction of the less dense, hydrophobic, resin treated surface of the absorbent web when the web is subjected to pressure in use. Rewetting or flooding of the resin treated surface 13(b) of the web is therefore, minimized, at least until the full absorptive capacity of the untreated hydrophilic portion 13(a) of the web has been exhausted.

As should be apparent from the forgoing description, an absorbent web of the type herein described is particularly well suited to producing a strong, absorbent disposable diaper having unique softness, texture and hand as well as favorable surface dryness characteristics.

FIGS. 1A and 1B illustrate schematically the processing operations necessary to convert an absorbent fibrous web of the present invention into a disposable diaper having the aforementioned attributes in addition to favorable strike-through characteristics. The resin-stabilized fibrous web 1 is cut into individual pad segments 13 by means of a rotary cutter 11 having blades 14 secured at its periphery and a hard-surfaced anvil roll 12. The individual pad segments 13 are separated to a predetermined spacing by means well known in the art and fed between a layer of waterproof backsheet material 15 and a layer of topsheet material 16.

One material which has been found particularly suitable for use as a waterproof backsheet is a matte finish polyethylene having a weight of approximately 29,000 square inches per pound, such as is available from the Visqueen Division of the Ethyl Corporation of Terre Haute, Ind. Although glossy finish polyethylenes will function equally well as a moisture barrier to prevent wicking of absorbed liquids from the hydrophilic portion 13(a) of the absorbent pad 13 to the clothing of the wearer, the dull matte finish of the preferred backsheet contributes favorably to the unique softness, texture and hand of applicant's diaper.

In order to preserve the overall softness impresssion of a diaper of the present invention, the waterproof backsheet 15 is preferably adhered directly to the untreated surface of the absorbent pad 13 by means of a soft, pressure-sensitive, adhesive 17 applied to the innermost surface of the waterproof backsheet by means of one or more spray nozzles 18. One such adhesive found suitable for use in the present invention is Covinax 62 UFP, a polyvinyl acetate base copolymer adhesive available from the Franklin Chemical Company of Columbus, Ohio.

The topsheet 16 used in a preferred embodiment of the present invention exhibits fast strike-through characteristics when placed in contact with the resin treated surface 13(b) of an absorbent pad 13 of the present invention.

In general, a topsheet material 16 which exhibits a strike-through time of less than about 5 seconds when placed in contact with the resin treated surface of an absorbent pad of the present invention will produce satisfactory results. This is determined by gently pouring 5 cubic centimeters of a 1 percent sodium chloride solution adjusted to a surface tension of 45 dynes per centimeter through a 1 inch diameter orifice in a 4 X 4 X ⅜ inch thick stainless steel plate placed over a 4 X 4 inch sample of the topsheet material superposed on a 4 X 4 inch sample of the resin treated absorbent core so that the topsheet is in contact with the resin treated surface of the absorbent core and measuring the amount of time required for the solution to pass through the topsheet and into the absorbent core.

Low density, high loft, hydrophobic topsheet materials are generally preferred in order to provide both improved strike-through and surface dryness qualities in a disposable diaper of the present invention. Excellent results are achievable using, for example, non-woven, needle punched polyester fabrics having a density of about 0.05 grams per cubic centimeter as measured under a load of 20 grams per square centimeter. One such material which has proven highly satisfactory in this service is a non-woven, 2¼ ounce per square yard, needle punched fabric made with 3 denier polyester staple and having a caliper of approximately 0.09 inches, such as is available from Troy Mills of Troy, N.H. The invention can also be practiced with similarly good results by the use of materials such as: a non-woven, needle punched fabric made with 6 denier polyester staple and having a caliper of approximately 0.11 inches, such as Troy Mills Code No. 3001–007500, also available from Troy Mills; or a non-woven, needle punched fabric made with 6 denier type 209 polyester staple and having a caliper of either 0.08 or 0.09 inches, such as Stearns & Foster grade O or grade K material, available from the Stearns & Foster Company of Lockland, Ohio. In the alternative, a less expensive material such as Webline No. SW-269-3, available from the Kendall Company of Walpole, Mass., may be utilized. The latter material has a basis weight of approximately 22 grams per square meter, a density of approximately 0.16 grams per cubic centimeter as measured under a load of 20 grams per square centimeter, and is comprised of 1.5 denier rayon fibers which are hydrophilic in nature. One surface of the Webline material is imprinted by the manufacturer with Rohm and Haas HA-8 binder in a diamond-shaped pattern constituting approximately 25 percent of the web's surface to impart a degree of hydrophobicity to the material. The Webline material, although comparable, from a strike-through standpoint, to the preferred topsheet materials cited earlier herein is less desirable than the preferred materials from a surface dryness standpoint. This is due to the higher density, i.e., the smaller capillary size, of the Webline material relative to the resin treated surface 13(b) of the absorbent pad 13 and the hydrophilic nature of the untreated portions of the Webline material which tend to absorb and retain moisture deposited thereon.

One novel and unique feature to be emphasized in connection with a disposable diaper of the present invention, however, is that the surface dryness obtainable by employing any of the suggested fast strike-through topsheet materials, whether hydrophobic or hydrophilic in nature, in combination with a resin treated absorbent pad of the present invention is at least equal to and is normally superior to that of prior art disposable diaper structures employing hydrophobic topsheets in combination with hydrophilic absorbent cores, while the strike-through characteristics thereof are markedly superior.

The improved surface dryness is attributed to the liquid partitioning properties of the hydrophobic resin treated surface 13(b) which is located immediately adjacent the topsheet 16. The aforementioned liquid partitioning properties are due not only to the hydrophobic nature of the resin treated surface 13(b), but also to the favorable density and capillary gradients which exist between the resin treated portion 13(b) and the untreated portion 13(a) of the absorbent pad 13. These factors operate to transmit fluids deposited on the resin treated portion 13(b) rapidly into the untreated portion 13(a) of the pad and to retain the absorbed fluids therein, at least until the absorptive capacity of the untreated portion of the pad has been exhausted. Because an absorbent pad 13 of the present invention combines the ability to absorb and partition moisture within a single, unitary structure, greater flexibility than has heretofore been possible is permitted in the selection of topsheet materials. Hence topsheet materials exhibiting optimum strike-through characteristics may be employed in combination with an absorbent pad 13 of the present invention without producing an unsatisfactory surface dryness condition, such as would be the case if such topsheet materials were placed directly over a non-resin treated hydrophilic core. Accordingly, an advantage inherent in applicants' structure is that it eliminates the need to compromise favorable strike-through characteristics in order to provide satisfactory surface dryness characteristics, a problem apparent in prior art disposable diaper structures.

The ability to combine fast strike-through and satisfactory surface dryness characteristics in a single structure permits the elimination of gasketing means used in prior art disposable diapers to prevent liquid run-off along the lateral edge portions of the diaper. The fast strike-through characteristic of a diaper of the present invention permits fluids deposited on the surface of the topsheet 16 to be transmitted into the absorbent pad 13 before substantial run-off from the surface of the topsheet is allowed to take place.

Another factor central to the elimination of gasketing means at the lateral edge portions of a disposable diaper of the present invention lies in the unique softness produced by bonding the untreated portion 13(a) of the absorbent pad 13 directly to the waterproof backsheet 15. The unique softness of a diaper of the present invention in combination with an absorbent pad 13 having sufficient strength to resist tearing and shredding in use permits better compliance when the structure is applied to the body of the wearer, thereby providing better fit and hence better containment of fluids deposited on the topsheet 16.

Figure 4:
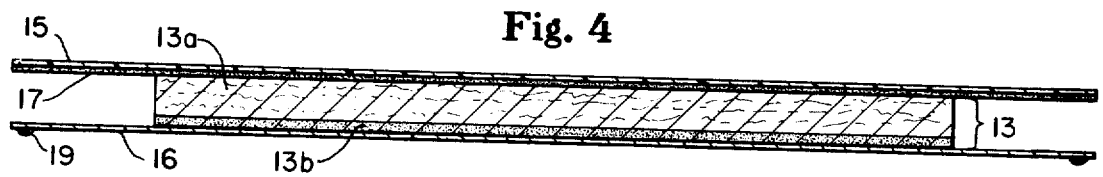
FIG. 4 is an enlarged simplified schematic illustration, taken along section line 4—4 in FIG. 1A, illustrating the condition of the absorbent fibrous web shown in FIGS. 2 and 3 after compression of the structure and prior to total encapsulation thereof between the waterproof backsheet adhered to its uppermost surface and the topsheet adjacent its lowermost surface.

FIG. 4 is an enlarged schematic illustration taken along section line 4—4 in FIG. 1A. FIG. 4 depicts the condition of the absorbent pad 13 after calendering and the position of the waterproof backsheet 15 in relation to the topsheet 16. Beads of adhesive 19 at the lateral edge portions of the topsheet 16 are applied by means of a pair of glue applicators 20 located at the lateral edge portions of the topsheet. The beads of adhesive 19 are preferably comprised of a hot melt adhesive such as No. 2933 available from the National Starch Company of Plainfield, N.J. The beads of adhesive 19 are used to secure the lateral edge portions of the diaper formed by the overlapping edge portions of the backsheet 15 and the topsheet 16 to the surface of the topsheet.

Figure 5:
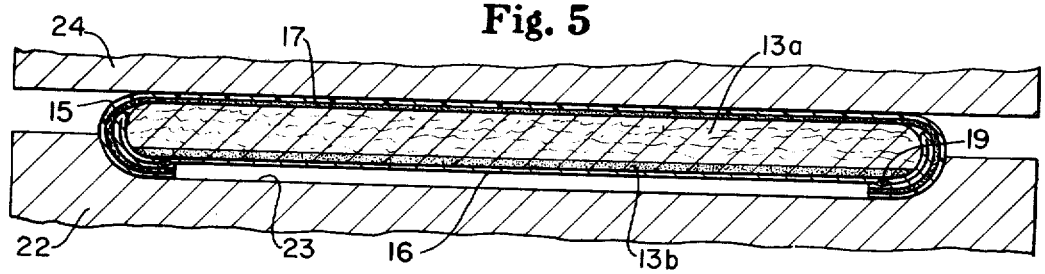
FIG. 5 is an enlarged simplified schematic illustration of a disposable diaper of the present invention, taken along section line 5—5 in FIG. 1A, illustrating the condition of the structure after the lateral edge portions of the topsheet have been secured to the lateral edge portions of the waterproof backsheet and the resulting lateral edge portions of the diaper have been folded back upon and secured to the surface of the topsheet.

The lateral edges of the assemblage shown in FIG. 4 are brought into overlapping relation with the topsheet by passing the assemblage between a pair of plows 21 located at the lateral edges thereof. The assemblage is then passed between a pair of hard-surfaced rolls 22 and 24 to secure the overlapping portions of the topsheet 16 and the backsheet 15 together as well as to secure the lateral edge portions of the assemblage to the face of the topsheet 16 by means of beads of adhesive 19. In addition, the topsheet 16 is secured to the backsheet 15 in the area between the absorbent pads 13. This is accomplished, in a preferred embodiment, by providing recessed areas 23 along the periphery of roll 22. The recessed areas 23 are of the same basic shape as the absorbent pads 13 and are so positioned along the periphery of roll 22 that the lateral edge portions of the absorbent pads are subjected to compression between rolls 22 and 24 to secure the assemblage together. This is best illustrated in FIG. 5. The areas between adjacent absorbent pads 13, on the other hand, are contacted by the non-recessed portions 25 of roll 22, which, in cooperation with the hardsurfaced roll 24, secure the topsheet 16 directly to the backsheet 15 and the lateral edge portions of the laminate thus formed to the face of the topsheet by means of beads of adhesive 19.

Securing the lateral edge portions of the diaper to the topsheet 16 in the manner illustrated in FIG. 5 serves to encapsulate the lateral edge portions of the absorbent pad 13, thereby preventing wicking of fluids absorbed in the absorbent pad from its lateral edge portions. This construction is preferred, since the waterproof backsheet 15 prevents wetting of clothing which comes in contact with the lateral edge portions of the diaper. Since overlapping the waterproof backsheet 15 onto the surface of the diaper is designed to prevent wicking from the absorbent core rather than run-off from the topsheet in a diaper of the present invention, the amount of overlap of the backsheet onto the surface of the topsheet 16 is preferably minimized to minimize contact between the backsheet and the wearer's skin, thereby improving wearer comfort.

In an alternate embodiment of the present invention, contact between the waterproof backsheet 15 and the wearer's skin can be completely eliminated by allowing the overlapping portions of the backsheet 15 and the topsheet 16 to extend horizontally at the edges of the diaper. In such an embodiment, however, it is generally desirable to size or otherwise make impervious to moisture by means well known in the art the lateral edge portions of the topsheet 16 to prevent wicking of absorbed fluids from the lateral edge portions of the absorbent pad 13.

Similar measures are also generally desirable with respect to the end portions of the topsheet 16 in both embodiments of the diaper disclosed herein to prevent wicking of absorbed fluids from the absorbent pad 13 along the end portions of the diaper.

The balance of the diaper converting operation is illustrated schematically in FIG. 1B. The absorbent pads 13, secured in a spaced relation by means of the web of waterproof backsheet material 15 and the web of topsheet material 16, are passed as a diaper web through tape applying apparatus well known in the art and shown schematically as 26, where a pressure-sensitive tape structure 27 suitable for holding the diaper in place on the wearer is applied at the lateral edge portions of the diaper web adjacent each absorbent pad 13.

Figure 6:
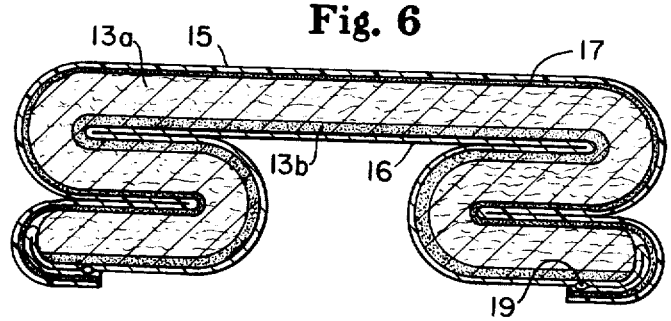
FIG. 6 is an enlarged simplified schematic illustration of a disposable diaper of the present invention, taken along section line 6—6 in FIG. 1B, showing a preferred configuration of the diaper in the finished state.

Following application of a pair of tape structures 27 for each absorbent pad 13, the diaper web is passed through folding apparatus well known in the art and shown schematically as 28 in FIG. 1B, whereby the diaper web, including the absorbent pads 13, is caused to assume the general configuration illustrated in FIG. 6.

Upon completion of the folding operation, the diaper web is passed between a rotary knife 29 having blades 30 secured at its periphery and a hard-surfaced anvil roll 31 where the web is cut in register between absorbent pads 13 to form individual disposable diapers 32 of the present invention.

It is to be understood that the forms of the invention herein illustrated and described are to be taken as preferred embodiments. Various modifications to the structures disclosed herein and to the method of producing said structures will be apparent to those skilled in the art without departing from the spirit or scope of the invention as defined in the attached claims.

Having thus defined and described the invention, what is claimed is:

1. A unitary, soft, reinforced, body fluid absorbent web suitable for use as an absorbent core in a disposable diaper, said web having a means for the rapid transport of body fluids throughout the web comprising a mass of entangled, hydrophilic fibers, the fibers on the surface thereof oriented toward the wearer's body having a coating of a hydrophobic, film-forming material thereon, the surface of said absorbent web containing said coated hydrophilic fibers exhibiting a lower density than the portions of said web containing uncoated hydrophilic fibers, thereby providing a capillary size gradient favorable to the transmission of liquid from the surface of said web containing said coated fibers to the portions of said web containing said uncoated fibers, said absorbent web having an overall density between about 0.09 grams per cubic centimeter and about 0.13 grams per cubic centimeter, as measured under a load of 20 grams per square centimeter, and a wet tensile strength of at least about 0.5 pounds per inch of width.

2. The absorbent web of claim 1, having a basis weight between about 85 grams per square meter and about 516 grams per square meter.

3. A unitary, soft, reinforced, body fluid absorbent web for use adjacent a body fluid discharge area and exhibiting improved dryness on the surface thereof oriented toward the wearer's body, said web having a means for the rapid transport of body fluids throughout the web comprising a mass of entangled, hydrophilic fibers, the fibers on one surface thereof having a cured coating of a hydrophobic, film-forming material thereon, said absorbent web having an overall density between about 0.07 grams per cubic centimeter and about 0.15 grams per cubic centimeter, as measured under a load of 20 grams per square centimeter, the density of the coated surface of said web being less than the density of the uncoated portions thereof, thereby providing a capillary size gradient favorable to the transmission of liquid from the coated surface of said web to the uncoated portions thereof.

4. The absorbent web of claim 3, wherein the hydrophobic, film-forming material is comprised of a resin having a glass transition temperature between about −15°C and about +35°C.

5. The absorbent web of claim 4, wherein said hydrophobic film-forming material is comprised of a styrene-butadiene resin.

6. The absorbent web of claim 4, said web containing between about 5 grams and about 16 grams of resin solids per square meter of absorbent web.

7. The absorbent web of claim 6, said web having a wet tensile strength of at least about 0.5 pounds per inch of width.

8. The absorbent web of claim 2, wherein said mass of entangled, hydrophilic fibers is comprised of airfelt.

9. The absorbent web of claim 3, wherein the thickness of the uncoated portion of the mass of entangled, hydrophilic fibers comprises at least about 50 percent of the total thickness of said web.

10. The absorbent web of claim 2, said web having a basis weight between about 85 grams per square meter and about 516 grams per square meter.

* * * * *

UNITED STATES PATENT AND TRADEMARK OFFICE
CERTIFICATE OF CORRECTION

PATENT NO. : 3,955,577
DATED : May 11, 1976
INVENTOR(S) : DALE A. GELLERT, KENDALL L. HARDEN and JOHN R. NOEL It is certified that error appears in the above-identified patent and that said Letters Patent are hereby corrected as shown below:

Column 8, line 5, "force" should read -- forced --.

Column 8, line 27, "centimeters" should read -- centimeter --.

Column 12, line 13, "placed" should read -- applied --.

Claim 8, column 14, line 65, "Claim 2" should read -- Claim 3 --.

Claim 10, column 15, line 3, "Claim 2" should read -- Claim 3 --.

Signed and Sealed this

Tenth Day of May 1977

[SEAL]

Attest:

RUTH C. MASON
Attesting Officer

C. MARSHALL DANN
Commissioner of Patents and Trademarks